United States Patent [19]

Axen

[11] 4,223,157
[45] Sep. 16, 1980

[54] 6-KETO-ωARYL-PGE₁ COMPOUNDS

[75] Inventor: Udo F. Axen, Plainwell, Mich.

[73] Assignee: The Upjohn Company, Kalamazoo, Mich.

[21] Appl. No.: 70,228

[22] Filed: Aug. 27, 1979

Related U.S. Application Data

[60] Division of Ser. No. 829,679, Sep. 2, 1977, which is a continuation-in-part of Ser. No. 755,675, Dec. 30, 1976, abandoned.

[51] Int. Cl.² .............................................. C07C 177/00
[52] U.S. Cl. ...................................... 560/53; 562/464; 260/410; 260/410.9 R; 260/410.5; 260/410.6; 260/413

[58] Field of Search .......................... 560/53; 562/464; 260/410, 410.5, 410.6, 410.9, 413

[56] References Cited
PUBLICATIONS

Derwent Abstract, 50721 A/28, JS 3063-358, TEIJ, 19-11-76.

*Primary Examiner*—Paul J. Killos
*Attorney, Agent, or Firm*—Robert A. Armitage

[57] ABSTRACT

Prostaglandin E (PGE)-type derivatives and analogs having a 6-keto feature are disclosed, including processes for preparing them and the appropriate intermediates, said derivatives having pharmacological activity.

47 Claims, No Drawings

6-KETO-ωARYL-PGE$_1$ COMPOUNDS

DESCRIPTION

CROSS REFERENCE TO RELATED APPLICATION

This application is a divisional application of copending application Ser. No. 829,679 filed Sept. 2, 1977, now pending issuance; which is a continuation-in-part of Ser. No. 755,675, filed Dec. 30, 1976, now abandoned.

BACKGROUND OF THE INVENTION

The present invention relates to novel 6-1 -keto- ω-aryl-PGE$_1$ compounds which are useful agents for the induction of prostacyclin-like pharmacological effects. Accordingly, these compounds are useful for pharmacological purposes for which prostacyclin and related substances are employed. The essential material constituting disclosure of the preparation and use of these novel compounds is incorporated here by reference from Ser. No. 829,679, filed Sept. 2, 1977.

SUMMARY OF THE INVENTION

The present invention particularly provides a compound of the formula

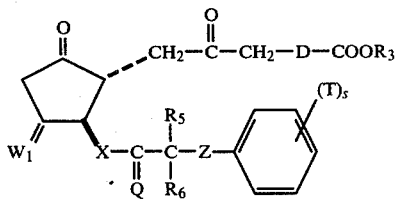

wherein W$_1$ is α-OH:β-H, α-H:β-OH, α-H:β-H, methylene, or α-CH$_2$OH:β-H;
wherein R$_3$ is
(a) hydrogen,
(b) alkyl of one to 12 carbon atoms, inclusive.
(c) cycloalkyl of 3 to 10 carbon atoms, inclusive,
(d) aralkyl of 7 to 12 carbon atoms, inclusive,
(e) phenyl,
(f) phenyl substituted with one, 2 or 3 chloro or alkyl of one to 4 carbon atoms, inclusive,
(g) p-[p-(acetamido)benzamido]phenyl,
(h) p-(benzamido)phenyl,
(i) p-(acetamido)phenyl,
(j) p-hydroxyphenylurea,
(k) p-hydroxybenzaldehyde semicarbazone,
(l) β-naphthyl,
(m) -CH(R$_{11}$)-CO-R$_{10}$.
wherein Q is keto, α-H:β-H, α-OH:β-R$_8$, or α-R$_8$:β-OH, wherein R$_8$ is hydrogen, methyl or ethyl.
wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro and the further proviso that neither R$_5$ nor R$_7$ is fluoro when Z is oxa (—O—). wherein Z represents an oxa atom (—O—) or C$_j$H$_{2j}$ wherein C$_j$H$_{2j}$ is a valence bond or alkylene of one to 9 carbon atoms, inclusive, with one to 6 carbon atoms, inclusive between CR$_5$R$_6$— and the (PH); wherein (PH) is phenyl or phenyl substituted by (T)s, wherein T is alkyl of one to 4 carbon atoms, inclusive, fluoro, chloro, trifluoromethyl, or —OR$_7$— wherein R$_7$ is alkyl of one to 4 carbon atoms, inclusive, and wherein s is zero, one, 2 or 3, with the proviso that not more than two T's are other than alkyl and when s is 2 or 3 the T's are either the same or different;
wherein X is
(1) trans—CH=CH—
(2) cis—CH=CH—
(3) —C≡C— or
(4) —CH$_2$CH$_2$—
wherein D is
(1) —(CH$_2$)$_d$—C(R$_2$)$_2$—
(2) —CH$_2$—O—CH$_2$—Y— or
(3) —CH$_2$CH=CH— wherein d is zero to 5, R$_2$ is hydrogen, methyl or fluoro, being the same or different with the proviso that one R$_2$ is not methyl when the other is fluoro, and Y is a velence bond, —CH$_2$— or —(CH$_2$)$_2$—, and the pharmacologically acceptable salts thereof when R$_3$ is hydrogen.

With regard to the divalent substituents described above, e.g., Q and W$_1$, these divalent radicals are defined as α-R$_i$:β-R$_j$, wherein R$_i$ represents a substituent of the divalent moiety of the alpha configuration with respect to the cyclopentane ring and R$_j$ represents a substituent of the divalent moiety of the beta configuration with respect to the cyclopentane ring. Accordingly, when Q is defined as α-OH:β-R$_8$, the hydroxy of the Q moiety is in the alpha configuration, i.e. as in prostacyclin, and th R$_8$ substituent is in the alpha configuration. Not all carbon atoms to which such divalent moieties are attached represent asymmetric centers. For example, when both valence bonds are to hydrogen, (e.g., W$_1$ or Q is α-H:β-H), then no asymmetric center is present.

DESCRIPTION OF THE PREFERRED EMBODIMENTS

The present invention particularly relates to the following chemical compounds:
16phenoxy-17, 18, 19, 20-tetranor-6,15-diketo-PGE$_1$;
16-phenoxy-17,18,19,20-tetranor-6-keto-PGE$_1$;
6-keto-16-phenoxy-17,18,19,20-tetranor-PGE$_1$;
6-keto-16-phenoxy-17,18,19,20-tetranor-PGE$_1$;
6keto-16-phenoxy-17,18,19,20-tetranor-PGE$_1$, p-phenylphenacyl ester;
6-keto-16-phenoxy-17,18,19,20-tetranor-PGE$_1$, p-(acetamidobenzamido)phenyl ester;
6-keto-16-phenoxy-17,18,19,20-tetranor-PGE$_1$, p-benzaldehyde semicarbazone ester;
16,16-demethyl-6-keto-16-phenoxy-17,18,19,20-tetranor-PGE$_1$;
16,16-dimethyl-6-keto-16-phenoxy-17,18,19,20-tetranor-PGE$_1$;
16,16-diemthyl-6-keto-16-phenoxy-17,18,19,20-tetranor-PGE$_1$, p-phenylphenacyl ester;
16,16-dimethyl-6-keto-16-phenoxy-17,18,19,20-tetranor-PGE$_1$, p-(acetamidobenzamido)-phenyl ester;
16,16-dimethyl-6-keto-16-phenoxy-17,18,19,20-tetranor-PGE$_1$, p-benzaldehyde semicarbazone ester;
16-phenyl-17,18,19,20-tetranor-6-keto-PGE$_1$;
17-phenyl-18,19,20-trinor-6-keto-PGE$_1$;
15(S)-15-methyl-6-keto-16-phenoxy-17,18,19,20-tetranor-PGE$_1$;
15(S)-15-methyl-6-keto-16-phenoxy-17,18,19,20-tetranor-PGE$_1$, a p-phenylphenacyl ester;

15(S)-15-methyl-6-keto-16-phenoxy-17,18,19,20-tetranor-PGE$_1$, p-(p-acetamidobenzamido)-phenyl ester;
15(S)-15-methyl-6-keto-16-phenoxy-17,18,19,20-tetranor-PGE$_1$, benzaldehyde semicarbazone ester;
15(R)-15-methyl-6-keto-16-phenoxy-17,18,19,20-tetranor-PGE$_1$;
6-keto-13,14-didehydro-16-phenoxy-17,18,19,20-tetranor PGE$_1$;
6-keto-13,14-didehydro-(15R)-16-phenoxy-17,18,19,20-tetranor-PGE$_1$;
6-keto-13,14-dihydro-16-phenoxy-17,18,19,20-tetranor-PGE$_1$;
2,2-difluoro-6-keto-16-phenoxy-17,18,19,20-tetranor-PGE$_1$, methyl ester;
2,2-difluoro-16,16-dimethyl-6-keto-16-phenoxy-17,18,19,20-tetranor-PGE$_1$, methyl ester;
2,2-difluoro-(15S)-15-methyl-6-keto-16-phenoxy-17,18,19,20-tetranor-PGE$_1$, methyl ester;
2,2-difluoro-13,14-didehydro-6-keto-16-phenoxy-17,18,19,20-tetranor-PGE$_1$, methyl ester; and
2,2-difluoro-13,14-dihydro-6-keto-16-phenoxy-17,18,19,20-tetranor-PGE$_1$, methyl ester.

I claim:
1. A compound of the formula

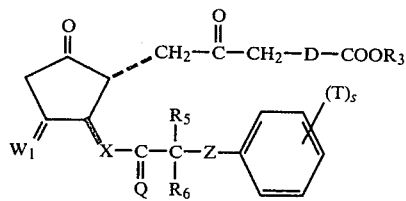

wherein W$_1$ is α-OH:β-H, α-H:β-OH, α-H:β-H, methylene, or α-CH$_2$OH:β-H;
wherein R$_3$ is
(a) hydrogen
(b) alkyl of one to 12 carbon atoms, inclusive.
(c) cycloalkyl of 3 to 10 carbon atoms, inclusive,
(d) aralkyl of 7 to 12 carbon atoms, inclusive,
(e) phenyl,
(f) phenyl substituted with one, 2 or 3 chloro or alkyl of one to 4 carbon atoms, inclusive,
(g) p-[p-(acetamido)benzamido]phenyl,
(h) p-(benzamido)phenyl,
(i) p-(acetamido)phenyl,
(j) —NH—CO—NH$_2$,
(k) CH═N—NH—CO—NH$_2$,
(l) β-naphthyl,
(m) —CH(R$_{11}$)—CO—R$_{10}$,
wherein Q is keto, α-H:β-H, α-OH:β-R$_8$, or α-R$_8$:β-OH, wherein R$_8$ is hydrogen, methyl or ethyl,
wherein R$_5$ and R$_6$ are hydrogen, alkyl of one to 4 carbon atoms, inclusive, or fluoro, being the same or different, with the proviso that one of R$_5$ and R$_8$ is fluoro only when the other is hydrogen or fluoro and the further proviso that neither R$_5$ nor R$_6$ is fluoro when Z is oxa (—O—); wherein Z represents an oxa atom (—O—) or C$_j$H$_{2j}$ wherein C$_j$H$_{2j}$ is a valence bond or alkylene of one to 9 carbon atoms, inclusive, with one to 6 carbon atoms, inclusive between CR$_5$R$_6$— and the (Ph); wherein (Ph) is phenyl or phenyl substituted by (T)s,
wherein T is alkyl of one to 4 carbon atoms, inclusive, fluoro, chloro, trifluoromethyl, or —OR$_7$— wherein R$_7$ is alkyl on one to 4 carbon atoms, inclusive, and wherein s is zero, one, 2 or 3, with the proviso that not more than two T's are other than alkyl and when s is 2 or 3 the T's are either the same or different;
wherein X is
(1) trans—CH═CH—
(2) cis—CH═CH—
(3) —C≡C— or
(4) —CH$_2$CH$_2$—
wherein D is
(1) —(CH$_2$)$_d$—C(R$_2$)$_2$—
(2) —CH$_2$—O—CH$_2$—Y— or
(3) —CH$_2$CH═CH— wherein d is zero to 5, R$_2$ is hydrogen, methyl or fluoro, being the same or different with the proviso that one R$_2$ is not methyl when the other is fluoro, and Y is a valence bond, —CH$_2$— or —(CH$_2$)$_2$—, and the pharmacologically acceptable salts thereof when R$_3$ is hydrogen.

2. A compound according to claim 1 wherein W$_1$ is α-OH:β-H.
3. A compound according to claim 2 wherein D is —(CH$_2$)d—C(R$_2$)$_2$— wherein d and R$_2$ are as defined in claim 2.
4. A compound according to claim 3 wherein D is —(CH$_2$)$_3$—.
5. A compound according to claim 4 wherein X is trans—CH═CH—.
6. A compound according to claim 5 wherein Q is oxo.
7. 16-Phenoxy-17,18,19,20-tetranor-6,15-diketo-PGE$_1$, a compound according to claim 6.
8. A compound according to claim 5 wherein Q is α-OH:β-R$_8$, wherein R$_8$ is hydrogen, methyl or ethyl.
9. A compound according to claim 8 wherein R$_8$ is hydrogen.
10. 16-Phenoxy-17,18,19,20-tetranor-6-keto-PGE$_1$, a compound according to claim 9.
11. 6-Keto-16-phenoxy-17,18,19,20-tetranor-PGE$_1$, methyl ester, a compound according to claim 9.
12. 6-Keto-16-phenoxy-17,18,19,20-tetranor-PGE$_1$, sodium salt, a compound according to claim 9.
13. 6-Keto-16-phenoxy-17,18,19,20-tetranor-PGE$_1$, p-phenylphenacly ester, a compound according to claim 9.
14. 6-Keto-16-phenoxy-17,18,19,20-tetranor-PGE$_1$, p-(acetamidobenzamido)phenyl ester, a compound according to claim 9.
15. 6-Keto-16-phenoxy-17,18,19,20-tetranor-PGE$_1$, p-hydroxybenzaldehyde semicarbazone ester, a compound according to claim 9.
16. 16,16-Dimethyl-6-keto-16-phenoxy-17,18,19,20tetranor-PGE$_1$, a compound according to claim 9.
17. 16,16-Demethyl-6-keto-16-phenoxy-17,19,19,20-tetranor-PGE$_1$, methyl ester, a compound according to claim 9.
18. 16,16-Dimethyl-6-keto-16-phenoxy-17,18,19,20-tetranor-PGE$_1$, p-phenylphenacyl ester, a compound according to claim 9.
19. 16,16-Dimethyl-6-keto-16-phenoxy-17,18,19,20-tetranor-PGE$_1$, p-(acetamidobenzamido)-phenyl ester, a compound according to claim 9.
20. 16,16-Dimethyl-6-keto-16-phenoxy, 17,19,19,20-tetranor-PGE$_1$, p-hydroxybenzaldehyde semi-carbazone ester, a compound according to claim 9.
21. 16-Phenyl-17,18,19,20-tetranor-6-keto-PGE$_1$, a compound according to claim 9.
22. 17-Phenyl-18,19,20-trinor-6-keto-PGE$_1$, a compound according to claim 9.

23. A compound according to claim 8 wherein $R_8$ is methyl.

24. 15(S)-15-Methyl-6-keto-16-phenoxy-17,18,19,20tetranor-PGE$_1$, a compound according to claim 23.

25. 15(S)-15-Methyl-6-keto-16-phenoxy-17,18,19,20-tetranor-PGE$_1$, p-phenylphenacyl ester, a compound according to claim 23.

26. 15(S)-15-Methyl-6-keto-16-phenoxy-17,18,19,20-tetranor-PGE$_1$, p-(p-acetamidobenzamido)-phenyl ester, a compound according to claim 23.

27. 15(S)-15-Methyl-6-keto-16-phenoxy-17,18,19,20-tetranor-PGE$_1$, p-hydroxybenzaldehyde semicarbazone ester, a compound according to claim 23.

28. A compound according to claim 5 wherein Q is $\alpha$-$R_8$:$\beta$-OH, wherein $R_8$ is hydrogen, methyl or ethyl.

29. (15R)-15-Methyl-6-keto-16-phenoxy-17,18,19,20-tetranor-PGE$_1$, a compound according to claim 28.

30. A compound according to claim 4 wherein X is —C≡C—.

31. A compound according to claim 30 wherein Q is $\alpha$-OH:$\beta$-$R_8$, wherein $R_8$ is hydrogen, methyl or ethyl.

32. 6-Keto-13,14-didehydro-16-phenoxy-17,18,19,20-tetranor-PGE$_1$, a compound according to claim 31.

33. A compound according to claim 30 wherein Q is $\alpha$-$R_8$:$\beta$-OH, wherein $R_8$ is hydrogen, methyl or ethyl.

34. 6-Keto-13,14-didehydro-(15R)-16-phenoxy-17,18,19,20-tetranor-PGE$_1$, a compound according to claim 33.

35. A compound according to claim 4 wherein X is —CH$_2$CH$_2$—.

36. 6-Keto-13,14-dihydro-16-phenoxy-17,18,19,20-tetranor-PGE$_1$, a compound according to claim 35.

37. A compound according to claim 3 wherein D is —(CH$_2$)$_2$—CF$_2$—.

38. A compound according to claim 37 wherein X is trans—CH=CH—.

39. A compound according to claim 38 wherein Q is $\alpha$—OH:$\beta$—H.

40. 2,2-Difluoro-6-keto-16-phenoxy-17,18,19,20-tetranor-PGE$_1$, methyl ester, a compound according to claim 39.

41. 2,2-Difluoro-16,16-dimethyl-6-keto-16-phenoxy-17,18,19,20-tetranor-PGE$_1$, methyl ester, a compound according to claim 39.

42. A compound according to claim 38 wherein Q is $\alpha$—OH:$\beta$—CH$_3$.

43. 2,2-Difluoro-(15S)-15-methyl-6-keto-16-phenoxy-17,18,19,20-tetranor-PGE$_1$, methyl ester, a compound according to claim 42.

44. A compound according to claim 37 wherein X is —C≡C—.

45. 2,2-Difluoro-13,14-didehydro-6-keto-16-phenoxy-17,18,19,20-tetranor-PGE$_1$, methyl ester, a compound according to claim 44.

46. A compound according to claim 37 wherein X is —CH$_2$CH$_2$—.

47. 2,2-Difluoro-13,14-dihydro-6-keto-16-phenoxy-17,18,19,20-tetranor-PGE$_1$, methyl ester, a compound according to claim 46.

* * * * *

UNITED STATES PATENT OFFICE
CERTIFICATE OF CORRECTION

Patent No. 4,223,157               Dated    16 September 1980

Inventor(s)  Udo F. Axen

It is certified that error appears in the above-identified patent and that said Letters Patent are hereby corrected as shown below:

Column 1, lines 15-16, "6-1 -keto- ω-aryl-" should read -- 6-keto-ω-aryl- --; line 52, "p-hydroxyphenylurea," should read -- -NH-CO-NH$_2$, --; line 53, "p-hydroxybenzaldehyde semicarbazone," should read -- -CH=N-NH-CO-NH$_2$, --; line 62, "R$_5$ nor R$_7$" should read -- R$_5$ nor R$_6$ --;

Column 2, line 44 and 54, "PGE$_1$;" should read -- PGE$_1$, methyl ester; --;

Column 3, line 50, "CH=N-NH-CO-NH$_2$," should read -- -CH=N-NH-CO-NH$_2$, -- ; line 57, "one of R$_5$ and R$_8$" should read -- one of R$_5$ and R$_6$ --;

Column 4, line 43, "p-phenylphenacly ester," should read -- p-phenylphenacyl ester, --; line 53, "16,16-Demethyl-" should read -- 16,16-Dimethyl- --.

Signed and Sealed this

Eleventh Day of August 1981

[SEAL]

Attest:

Attesting Officer

GERALD J. MOSSINGHOFF

Commissioner of Patents and Trademarks